(12) United States Patent
Fleisher

(10) Patent No.: US 7,531,688 B2
(45) Date of Patent: May 12, 2009

(54) METHOD FOR RECOVERING UNREACTED ALCOHOL FROM BIODIESEL PRODUCT STREAMS BY FLASH PURIFICATION

(75) Inventor: Christian A. Fleisher, Tulsa, OK (US)

(73) Assignee: Orbitek, Inc., Tulsa, OK (US)

( * ) Notice: Subject to any disclaimer, the term of this patent is extended or adjusted under 35 U.S.C. 154(b) by 0 days.

(21) Appl. No.: 11/811,711

(22) Filed: Jun. 12, 2007

(65) Prior Publication Data

US 2008/0312468 A1 Dec. 18, 2008

(51) Int. Cl.
*C07C 69/66* (2006.01)
(52) U.S. Cl. .................................... 560/186
(58) Field of Classification Search .................. None
See application file for complete search history.

(56) References Cited

U.S. PATENT DOCUMENTS

| | | | |
|---|---|---|---|
| 4,164,506 A | 8/1979 | Kawahara et al. | 260/410.9 R |
| 4,695,411 A | 9/1987 | Stern et al. | 260/410.9 R |
| 4,698,186 A | 10/1987 | Jeromin et al. | 260/421 |
| 5,424,467 A | 6/1995 | Bam et al. | 554/216 |
| 5,525,126 A | 6/1996 | Basu et al. | 44/308 |
| 5,908,946 A | 6/1999 | Stern et al. | 554/167 |
| 6,174,501 B1 | 1/2001 | Noureddini | 422/189 |
| 6,538,146 B2 | 3/2003 | Turck | 554/169 |
| 7,045,100 B2 | 5/2006 | Ergün et al. | 422/129 |
| 7,126,032 B1 | 10/2006 | Aiken | 568/869 |
| 7,145,026 B2 | 12/2006 | Fleisher | 554/184 |
| 2006/0244005 A1 | 11/2006 | Chen | 257/122 |

OTHER PUBLICATIONS

English et al., Economic Feasibility of Producing Biodiesel in Tennessee, p. 50, published by Agri-Industry Modeling & Analysis Group (Dec. 2002).

*Primary Examiner*—Deborah D Carr
(74) *Attorney, Agent, or Firm*—Michael W. Ferrell

(57) ABSTRACT

A method for making fatty acid esters by reacting triglycerides with an excess of alcohol in a pressurized environment, where the unreacted alcohol component is separated from the reaction product by a flash purification techniques. In this manner, the pressure of the product stream is significantly reduced to vaporize unreacted alcohol, which is then condensed for later reuse. The invention provides a cost-effective and convenient mechanism to simultaneously recycle excess alcohol and to purify ester product and/or glycerol product streams.

22 Claims, 2 Drawing Sheets

METHOD FOR RECOVERING UNREACTED ALCOHOL FROM BIODIESEL PRODUCT STREAMS BY FLASH PURIFICATION

TECHNICAL FIELD

The present invention relates, in part, to a process for purifying reaction products formed in the synthesis of biodiesel ester reactors, and more particularly relates to a method for recovering and recycling unreacted alcohol from fatty acid ester product streams and glycerol product streams by flash purification. In a preferred embodiment, the invention reduces alcohol losses and promotes efficient operation through use of the latent heat of vaporization to pre-heat the feedstock.

BACKGROUND

Alkyl esters of fatty acids are commonly used as biodiesel fuel, and are a beneficial alternative fuel source compared to conventional fossil fuel sources. Fatty acid alkyl esters are produced by a transesterification reaction between triglycerides (animal fat and/or vegetable oil) and alcohol to form product esters and glycerol.

Transesterification processes for producing biodiesel alkyl esters are well known in the art. Historically, triglycerides in fats and oils have been methylated or otherwise esterified in a two-step process using an acidic catalyst, such as is described in the U.S. Pat. No. 4,695,411 to Stern et al., U.S. Pat. No. 4,698,186 to Jeromin et al., and U.S. Pat. No. 4,164,506 to Kawahara et al. Such processes included a pre-transesterification step, where fats/oils were reacted with alcohol in the presence of an acidic catalyst, and a subsequent transesterification step, where an alkaline/alcohol blend was added for the reaction completion. Transeterification processes employing alkaline catalysts, such as U.S. Pat. No. 5,525,126 to Basu et al., U.S. Pat. No. 5,908,946 to Stern et al., and U.S. Pat. No. 6,538,146 to Turck et al., are known in the art, as well.

The transesterification reaction is usually carried out in a reaction medium having a stoichiometric excess of alcohol, because this accelerates the production of useful esters. The excess unreacted alcohol present in the product mixture is distributed in both the ester rich light phase product and the glycerol rich heavy phase product. The excess alcohol in the product streams needs to be recovered so that the alcohol can be recycled to the process as a reactant, and to enhance the purity of the ester and glycerol product streams. Various methods of purifying the product streams and recovering excess alcohol have been described in the art.

U.S. Pat. No. 5,424,467 to Bam et al. describes a purification process in the manufacture of biodiesel esters whereby the unreacted alcohol in the glycerol rich product stream is removed by extractive distillation, and then the purified glycerol stream is contacted with the ester product stream in a liquid-liquid extraction unit to purify the ester product and to extract unreacted alcohol.

United States Patent Application Publication No. 2006/0244005 to Felly describes a process for making biodiesel where the product stream is cooled and allowed to separate into an ester rich phase and a glycerol rich phase. Alcohol vapor is recovered from the glycerol rich phase by boiling it under vacuum conditions by applying a vacuum pump. The alcohol is removed from the ester rich phase by washing with water. Additionally, alcohol vapor is recovered from the reactor and various holding tanks by applying a vacuum to the top of each unit. The vapor from the tanks and from the glycerol boiler is then sent to a condensing unit to recover the alcohol.

U.S. Pat. No. 7,126,032 to Aiken describes a process for purifying the glycerol rich product stream in biodiesel ester production, whereby the glycerol rich stream, which contains minor portions of alcohol and methyl ester, is heated to produce additional amounts of alcohol and glyceride. The stream is then sparged with nitrogen which strips the unreacted alcohol out of the stream. The unreacted alcohol vapor is subsequently condensed and collected.

U.S. Pat. No. 7,045,100 to Ergün et al. describes a biodiesel production system where the methyl ester product may be separated from the glycerol product by a filtration apparatus.

U.S. Pat. No. 6,174,501 to Noureddini relates to a process for making biodiesel esters where the glycerol rich product is decanted from the methyl ester rich product stream. The glycerol rich stream, which is at low pressure, is then sent through a deionizer to remove cations, and then sent to a flashing unit to remove methanol. The glycerol stream subsequently undergoes additional purification.

Other approaches for recovering excess alcohol have been described in the art, including a process where the ester rich phase is washed with water to extract the unreacted methanol, the water wash is combined with the glycerol rich phase, and then the methanol is distilled off from the combined glycerol/wash stream. See, English et al., Economic Feasibility of Producing Biodiesel in Tennessee, p. 50, published by Agri-Industry Modeling & Analysis Group (December 2002).

While the above described approaches facilitate the recovery of unreacted alcohol, they require substantial additional equipment and excessive energy expenditure. For example, the Felly reference described above uses numerous holding and decanting tanks, as well as expensive vacuum equipment to extract the unreacted alcohol. There accordingly exists a need for an efficient, cost-effective transesterification process whereby the unreacted alcohol component can be readily separated from the product ester or product glycerol streams, and be reused as a reactant component.

SUMMARY OF THE INVENTION

The present invention is directed, in part, to a method for reducing alcohol losses in biodiesel fuel manufacturing processes. In one aspect of the invention, there is provided a method for making biodiesel fatty acid esters comprising the steps of (a) reacting triglycerides with alcohol under pressure to produce a mixture containing fatty acid esters, glycerol, and unreacted alcohol; (b) separating the mixture into a glycerol enriched stream and a fatty acid ester stream, and maintaining at least one of these streams under pressure such that unreacted alcohol is present in the stream in liquid form; (c) forwarding at least one of the pressurized streams to a flash vessel and reducing the pressure of the stream to vaporize unreacted alcohol; and (d) condensing the alcohol vapor and sequestering it for subsequent reuse. The invention provides an efficient alcohol recovery system having low energy requirements which improves the overall economics of the biodiesel manufacturing process.

Further features and advantages of the present invention will become apparent from the discussion that follows.

BRIEF DESCRIPTION OF THE DRAWINGS

The invention is described in detail below with reference to the various Figures wherein like numerals designate similar parts and wherein.

DETAILED DESCRIPTION

Figure 1:
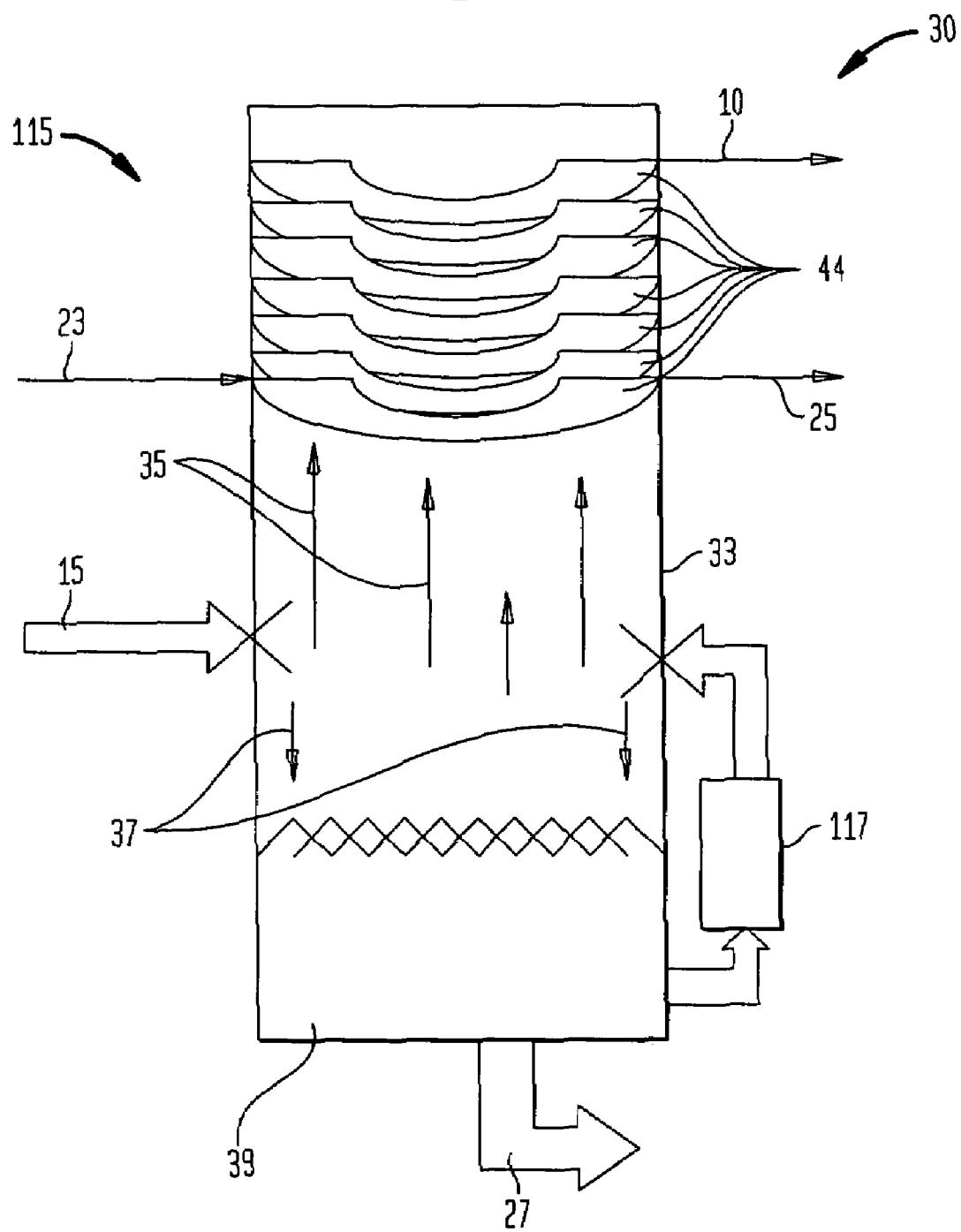
FIG. 1 is a schematic diagram illustrating a flash purification apparatus for recovering unreacted alcohol in a biodiesel manufacturing process.

The invention is described in detail below for purposes of illustration only. Modifications within the spirit and scope of the invention, set forth in the appended claims, will be readily apparent to one of skill in the art. As used herein, terminology and abbreviations have their ordinary meaning; for example, "psig" refers to pounds per square inches, gauge pressure.

Alcohol esters of fatty acids are used as an alternative fuel source, also called "biodiesel." The fatty acid esters are produced by a transesterification reaction between an alcohol and triglycerides. The transesterification reaction is illustrated schematically below:

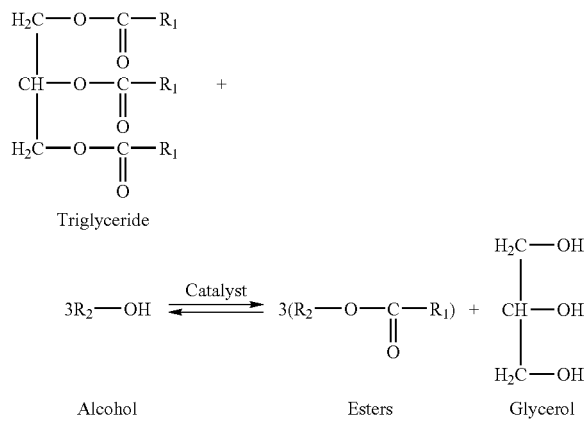

wherein $R_1$, stands for the hydrocarbyl moieties of the fatty acid constituents of vegetables oils or animal fats, and $R_2$ is a $C_1$-$C_4$ alkyl group.

As reflected in the above scheme, a triglyceride reacts with the alcohol and is converted stepwise to a diglyceride, a monoglyceride and finally to glycerol with a fatty acid alkyl ester liberated at each step, resulting in 3 ester molecules. In addition to the fatty acid alkyl esters formed in the reaction, glycerol is created as a by-product. The equilibrium of the reaction may be shifted to favor formation of the fatty acid esters by increasing the amount of alcohol reactant. Additionally, the formation of esters can be promoted by removal of the glycerol by product.

In accordance with the biodiesel manufacturing process of the present invention, the transesterification reaction occurs under pressurized conditions in the presence of a stoichiometric excess of alcohol. The reaction produces an intermediate mixture which includes fatty acid esters, glycerol, unreacted alcohol, and catalyst. The intermediate product mixture can be readily separated into an ester-rich phase and a glycerol-rich phase. Excess, unreacted alcohol is distributed in both the ester rich phase and the glycerol rich phase. Briefly, the unreacted alcohol is recovered by reducing the pressure of at least one of the intermediate streams in a flash vessel, causing the unreacted alcohol to flash off, and then condensing and collecting the alcohol for subsequent reuse. The recovery of unreacted alcohol in biodiesel systems is critical for the economics of the invention with respect to raw materials, as well as to provide product streams (glycerol, fatty acid esters) with enhanced purity.

The first step of the process of the invention comprises the transesterification reaction where the triglyceride and alcohol are reacted in the presence of a catalyst to produce an intermediate mixture comprising, as main components, fatty acid alkyl esters and glycerol.

As used herein, the term "triglyceride" has its ordinary meaning in the art as a glycerol having its hydroxy groups substituted by fatty acids. Examples of suitable triglyceride feedstock for use in the present invention include fats and oils of synthetic or natural origin, or mixtures thereof, comprising $C_4$-$C_{24}$, and in particular $C_{12}$-$C_{18}$ fatty acid groups, which may be straight or branched, saturated or unsaturated. Examples of such oils and fats include vegetable and/or animal sources such as corn oil, linseed oil, rape seed oil, olive oil, palm oil, canola oil, coconut oil, soybean oil, cottonseed oil, peanut oil, safflower oil, castor bean oil, tallow, lard, coca-butter, fish oils, combinations thereof, and the like. Preferably, the triglyceride feed stream introduced into the reaction zone is heated to a temperature of from about 150° F. to about 400° F. The feed stream is preferably substantially anhydrous, <500 ppm water and preferably has a free fatty acid content of 2% by volume or less.

Alcohols suitable for use in the present invention typically comprise any primary and secondary monohydric aliphatic alcohols having one to eight carbon atoms. Preferred alcohols for use in the transesterification process of the present invention are methanol, ethanol, propanol, isopropanol, and butanol, with methanol and ethanol being more preferred. Methanol is a particularly preferred alcohol because it has low cost, reacts quickly, dissolves the catalyst, and has a low boiling point.

The choice of catalyst used in the transesterification reaction is not particularly limited. Typical catalysts for the transesterification reaction include alkali metal salts. Alkali metal catalysts suitable for the transesterification reaction of the present invention include soluble NaOH, LiOH, KOH, carbonates and corresponding sodium and potassium alkoxides such as sodium methoxide, sodium ethoxide, sodium propoxide, sodium butoxide, and sodium methylate. Catalysts may also include insoluble metals embedded upon the inner surfaces of the reactor or parts thereof (i.e. surfaces of static mixing elements such as baffles). Examples of such catalysts include tin, lead, mercury, cadmium, zinc, titanium, zirconium, hafnium, boron, aluminum, phosphorus, arsenic, antimony, bismuth, calcium, magnesium, strontium, potassium, sodium, lithium, uranium. It should be noted that the catalyst may be a combination of soluble and insoluble catalysts.

The reactor in the present invention can be any type of reactor commonly used for transesterification reactions, examples of which include, but are not limited to, a reaction vessel having a stirrer or agitator, a vessel having a recirculation loop, or a static mixer within a pipe or a similar container. The reactor is preferably a tubular plug-flow reactor. Typically, the reactor is pressurized at a pressure of from 30 psi to 500 psi, and more typically operates at pressures of from 75 to 200 psi. The reaction temperature is typically in the range of from 150° F. to 500° F., and preferably from 200° F. to 400° F. High pressure in the tubular reactor creates high-shear, which in turn, emulsifies the triglycerides and the alcohol and forces a quasi single-phase liquid system (i.e. maintains alcohol in a liquid state) to facilitate a higher reaction rate. The reaction mixture is held in the reaction zone for a period of time sufficient to convert substantially all the triglyceride feedstock into fatty acid alkyl esters. It has been found that the process of the present invention can be completed in less than about three minutes.

The transesterification reaction produces an intermediate mixture which includes fatty acid esters, glycerol, remaining catalyst, and unreacted alcohol. This mixture readily separates into a ester-rich phase and a glycerol rich phase. The ester-rich portion and glycerol-rich portion may be separated by any means generally known in the art, e.g., gravity separation, decantation or centrifugation; means that separate components having different densities. Most preferably, the separation is achieved by means of hydroclone. A preferred hydroclone separator is model HY20 SS222ASY manufactured by CSI. A 2" hydroclone with two body extensions providing upflow and downflow outlets of 1" and a pressure drop of approximately 30 psi under typical conditions is suitable. U.S. patent application Ser. No. 11/789,824, filed Apr. 26, 2007, entitled "Apparatus and Method for Producing Biodiesel Fuel" (Attorney Docket No. BT-06-1), describes a suitable reaction process and liquid/liquid separation scheme for use with the alcohol recovery system of the present invention. The '824 application is incorporated herein in its entirety by reference. Also incorporated by reference is U.S. Pat. No. 7,145,026 to Fleisher which provides details as to reactants and processing parameters.

The unreacted alcohol is distributed in both the ester-rich portion and the glycerol-rich portion, where the majority of the alcohol is typically in the glycerol-rich portion. The glycerol-rich stream also contains a minor portion of ester product, and the ester-rich stream contains a minor portion of glycerol; that is, complete separation does not occur with the initial separation step.

The unreacted alcohol may be conveniently and economically recovered from the pressurized intermediate streams (ester rich and/or glycerol rich) by maintaining a suitable pressure in the stream, and flashing the pressurized stream by reducing the pressure and vaporizing the alcohol. Thus, the intermediate streams should not experience a significant pressure drop or a substantial decrease in temperature when the initial reaction product mixture is separated into the ester-rich and glycerol-rich streams, because the pressure and temperature of these streams drives the subsequent flash purification step. Generally, the pressure of the intermediate stream that is being purified (glycerol enriched and/or ester enriched) should be maintained above 30 psig, and more preferably above 75 psig, or above 125 psig. Upon entering the flash vessel, the intermediate stream generally experiences a pressure drop of more than 50 psi, and preferably undergoes a pressure drop of more than 100 psi. The temperature of the stream is typically maintained above the atmospheric boiling temperature of the alcohol, so that the alcohol is readily vaporized when it enters the flash purification unit. Typically, the temperature of the intermediate stream is in the range of from about 150° F. to 350° F., and more preferably from 200° F. to 280° F.

The invention enables the unreacted alcohol to be efficiently recovered from the system without expending significant energy or equipment costs, by using high pressure and high temperature from the reaction to drive the alcohol separation. According to the invention, either or both of the fatty acid ester rich stream or the glycerol rich stream may be forwarded to a flash purification vessel to recover the unreacted alcohol. Conveniently, the ester rich stream may be purified in one flash purification vessel, while the glycerol rich stream is purified in another vessel; alternative configurations are within the scope of the invention. The flash purification may be operative to remove at least 50 percent (volumetric) of the alcohol that is present in the stream which is forwarded to the flash unit, and preferably is operative to remove at least about 75 percent of the unreacted alcohol in the stream that is forwarded to the flash unit. In embodiments where both a fatty-acid ester-rich stream and a glycerol-rich stream are treated, the inventive method provides a biodiesel process which has less than 1 percent of overall alcohol loss. This is a significant improvement in alcohol recovery as compared to prior art processes.

The operation of a preferred embodiment of the flash purification unit is described with reference to FIG. 1 where the flash purification unit 30 includes a column 33 having a condensing unit 115 in the upper third of the column. The pressurized intermediate stream 15, (for instance a glycerol rich intermediate stream containing methanol reactant) enters the middle section of the column as a liquid at an initial pressure of about 140 to 190 psi and a temperature of from about 240-270° F. The column operates at a slight vacuum pressure, and the stream experiences a significant drop in pressure upon entering the flash vessel through a valve, causing alcohol vapor (shown schematically at 35) to flash out of the intermediate stream 15, and causing alcohol-depleted liquid (shown schematically at 37) to fall to the bottom and collect at reservoir 39. The alcohol vapor that is liberated from the intermediate stream is condensed in condensing unit 115 on a series of reflux coils with alcohol recovery trays 44. The reflux coils are cooled by a coolant stream 23 which enters the condensing unit 115 at a temperature generally in the range of from 50° F. to 100° F. The coolant exits the condenser at stream 10 having a higher temperature, generally by at least 50° F. The condensed alcohol is taken off of the column from the recovery trays as a warm liquid at stream 25 where it is combined with methanol/catalyst storage. The alcohol-depleted product stream is taken off of the flash unit at stream 27. The flash purification unit may include reboiler 117 to supply heat to the alcohol-depleted portion and further drive alcohol vaporization-so called "flash distillation" herein, because vaporization is driven by heat addition and pressure drop. The reboiler may share the same heat source as the reactor and, in any event, does not require substantial energy due to the significant pressure drop.

In some embodiments of the invention, the cooling stream 23 supplied to the reflux coils is the pre-reactor triglyceride feedstock stream which includes organic fats, oils, greases, and combinations thereof. The use of the reactant stream to condense the unreacted alcohol is advantageous because no energy is expended to cool the alcohol vapor, and it concurrently preheats the triglyceride reactant stream prior to entering the reactor. The triglyceride pre-reactor feedstock stream is preferably heated in the condenser by at least 25° F., by at least 50° F., and more preferably by at least 75° F. or more. Typically, the feedstock is preheated to temperatures of from 150° F. to 450° F.

It has been discovered that the alcohol condensation can be affected even using triglyceride component at ambient temperature. The ambient temperature coolant may pass through from 1 to 100 coils or more, if needed, in order to achieve the level of cooling needed to condense all of the evaporated alcohol. If necessary, higher quantities of triglyceride reactant than are needed for the reactor feed may be used as cooling fluid. In these circumstances, the excess coolant (which is not yet needed in the reactor) is sent through a radiator to cool before being sent back to storage. The alcohol vapors may be condensed into liquid alcohol which usually has a temperature of at least 120° F. The warm liquid alcohol may be recycled to the reactor or stored for later use. In this manner, the inventive method utilizes the enthalpy of the process streams to preheat the pre-reactor triglyceride feedstock, which further reduces the energy requirements and costs of the manufacturing process.

The flash distillation unit shown in FIG. 1 operates at a slight negative pressure due to the precipitation of methanol on the condensing unit. The vacuum conditions assist in pulling additional vaporized methanol toward the reflux coils. Typically, the flash distillation unit operates at a pressure of from −2 psig to −10 psig, and generally from about −4 to −6 psig. The temperature of the product stream should be maintained so that it is high enough that the alcohol which is remaining in the product stream will boil off from the product component at the operating pressure of the column. For example, lower alcohols will readily boil off of either biodiesel or glycerol streams at temperatures of from about 148° F. to 165° F. at atmospheric pressure. Additionally, when operating under a slight negative pressure, the boiling point of the alcohol can be reduced by about 5-10° F. The boiling point of methanol, for example, drops from about 163° F. (at atmospheric) to about 154° F. (at about −5 psig). Typically, the flash distillation column operates at a temperature of from 100° F. to 275° F., and preferably from 140° F.-170° F.

Figure 2:
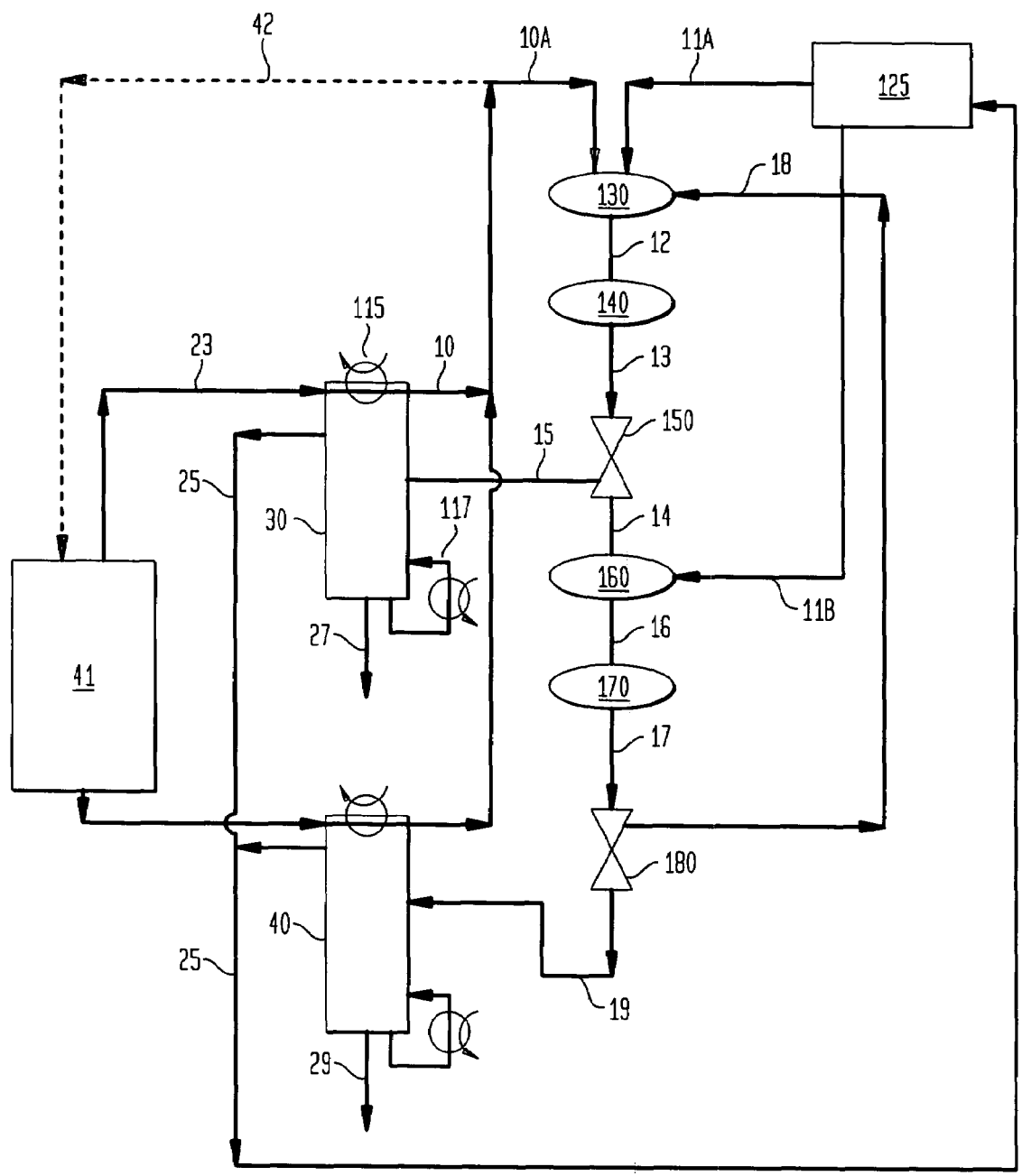
FIG. 2 is a flow diagram showing a transesterification process according to one embodiment of the present invention.

For clarification and illustration, a particularly preferred embodiment of the overall biodiesel ester production process of the invention will be described with reference to FIG. 2. The process of the invention is implemented by contacting a triglyceride stream 10A with an alcohol/catalyst solution feed stream 11A; both streams 10A and 11A have temperature of from about 150° C. to about 400° C. and pressures of from about 150 psig to about 400 psig. The triglyceride feedstock is preheated from heat exchange with methanol vapors in the methanol recovery process which is described in greater detail below.

Streams 10A, 11A, and 18, are mixed by mixer 130 to form mixture stream 12. Preferably, the flow of stream 12 is maintained at Reynolds numbers in the turbulent flow regime to enhance mixing. For a 1 inch inside diameter tubular reactor (0.65" wall), from about 5 fps to about 8 fps linear velocity is preferred. It should be noted that stream 18 is a recycle stream containing unreacted alcohol, glycerol, and fatty acid alkyl esters separated by hydroclone 180 from the final product. Stream 12 enters a first reaction zone, tubular reactor 140, where the triglyceride feedstock and alcohol are reacted in the presence of the catalyst to form an intermediate reaction mixture stream 13 comprising fatty acid alkyl esters, glycerol, unreacted triglyceride feedstock, catalyst and unreacted alcohol. Stream 13 is passed through hydroclone 150. The glycerol has a higher density than the fatty acid alkyl esters which results in a rapid and distinct separation. Therefore, the heavy phase stream 15, containing glycerol and some unreacted alcohol, is separated and removed from the bottom and transferred to a glycerol/alcohol flash purification unit 30.

The light phase stream 14, containing fatty acid alkyl esters and unreacted triglyceride feedstock, is combined with a fresh feed of alcohol/catalyst 11B in mixer 160 to form stream 16. It should be noted that the amount of the alcohol/catalyst solution in stream 11A is from about 10% to about 40% by volume of the total methanol/catalyst solution used in combined streams 11A and 11B. Preferably, the amount of alcohol-catalyst solution in stream 11A is at a ratio of about 2 parts by weight of alcohol/catalyst solution to about 10 parts by weight of triglyceride present in stream 10A; or, more particularly, a mole ratio of alcohol to triglyceride in mixer 130 is of from about 4:1 to about 8:1; and in any case preferably at least 3 or more. The total amount of catalyst to be used in the transesterification reaction ranges from about 0.2 to about 2 percent by weight, more preferably from about 0.25 to about 1.25 percent by weight, of triglyceride entering mixer 130.

Introducing fresh alcohol and catalyst into several reaction zones and removal of the produced glycerol from at least one of the reaction zones within a single reactor vessel allows for more efficient reaction control in terms of temperature and reactants/catalyst contact, and accordingly, provides for increased reaction rate and significantly lower residence time of the overall process. This, in turn, contributes to an overall cost-effective process that provides for a compact single structure comprising a plug-flow reactor, hydroclone inside a single vessel, which may utilize a single heat-exchanger medium. It also has been found that use of multiple feeds of fresh alcohol and catalyst into the reaction zones advantageously reduces the amount of alcohol reactant necessary to effect the reaction. It should be noted that the first transesterification step (i.e. first reaction zone) is preferably achieved in from about 20 seconds to about 30 seconds, whereas the second transesterification step (i.e., second reaction zone) is preferably achieved in from about 30 seconds to about 60 seconds.

In the second transesterification step, stream 16 is passed to the next reaction zone, tubular reactor 170 for further transesterification. Once the transesterification reaction in the second reaction zone proceeds to the desired conversion, the reaction mixture 17 is passed through hydroclone 180 to separate it into two phases. Heavy phase 18, containing glycerol, unreacted alcohol, and at least 20% or 30% by volume fatty acid alkyl esters, is recycled and mixed in mixer 130 with streams 10A and 11A. This layout provides for increased efficiency and allows for use of the biodiesel as a co-solvent in the process, utilizing a stream that would otherwise have to be discarded or substantially re-processed. Light phase 19, containing fatty acid alkyl esters and unreacted alcohol is removed from the hydroclone into flash purification unit 40, which may be similar or substantially identical to flash purification unit 30 and operates in substantially the same manner.

It should be noted that the pressure control may be achieved by use of pumps which supply raw material reactants from storage. Preferred pressures at the reactor inlet, stream 12, is about anywhere from about 175 psig to about 400 psig such as, for example, 220 psig, the most preferred pressure at the reactor outlet, stream 19, is about 150 psig, and the pressure drop across each hydroclone (150 and 170) is about 30 psig; for example, the pressure drops from 210 psig in stream 13 to 180 psig in streams 14 and 15; and from 180 psig in stream 17 to 150 psig in streams 18 and 19.

The unreacted methanol is removed from pressurized glycerol-rich stream 15 by flash distilling the stream in vessel 30 which operates at a pressure of about −5 psig due to the alcohol vapor condensing on coils in the upper portion of the column. The pressure drop vaporizes much of the methanol which is cooled by a condensing unit 115 located in the upper third of the column, and which uses the feedstock triglyceride stream 23 as coolant. The flash purification unit is also coupled to a reboiler 117 (same heat source as reactor) to further volatize any remaining methanol. The condensed, warm methanol is returned to the alcohol storage 125 via stream 25. The triglyceride coolant stream exiting the flash purification unit 10 is thereby preheated by heat exchange with the methanol. If needed, some of the preheated triglyceride stream can be returned to storage 41 via stream 42. The glycerol enriched streams 27, 29 are taken off as a product or sent forward to additional purification steps.

The purification of the biodiesel enriched product stream 19 proceeds in flash purification unit 40 similarly as that of stream 15 in unit 30. The methyl ester enriched product stream 29 is removed from the unit and taken off as product or sent to additional purification zones. The recovered methanol may likewise be sent back to storage 125 or returned to the reactor via stream 25.

While the invention has been described in connection with numerous examples, modifications to those examples within the spirit and scope of the invention will be readily apparent to those of skill in the art. In view of the foregoing discussion, relevant knowledge in the art and references including co-pending applications discussed above, the relevant disclosures of which are all incorporated herein by reference, further description is deemed unnecessary.

What is claimed is:

1. A method for recovering unreacted alcohol from biodiesel product streams formed in biodiesel ester reactors, said method comprising the steps of:
   a) reacting triglycerides in an excess of alcohol to produce an intermediate mixture comprising fatty acid esters, glycerol, and unreacted alcohol, wherein the reaction takes place in a reaction zone at a pressure of at least 30 psig and a temperature of at least 150° F.;
   b) separating the intermediate mixture into a glycerol enriched stream and a fatty acid ester enriched stream, where at least one of the streams is pressurized to at least 30 psig and includes unreacted alcohol in liquid form;
   c) forwarding at least one of the pressurized streams to a flash vessel, where the pressure of the stream is reduced and the temperature of the stream is maintained at a level such that unreacted alcohol in said stream is vaporized;
   d) condensing the alcohol vapor and sequestering the condensed alcohol from the forwarded stream; and
   e) recycling the condensed alcohol to the reaction zone such that the condensed alcohol is used as a reactant.

2. The method according to claim 1, wherein the flash vessel is operative to recover at least 50 percent (volumetric) of the unreacted alcohol that is present in the forwarded stream.

3. The method according to claim 1, wherein the flash vessel is operative to recover at least 75 percent (volumetric) of the unreacted alcohol that is present in the forwarded stream.

4. The method according to claim 1, wherein the pressure of the forwarded stream is reduced by at least 50 psig to vaporize the unreacted alcohol.

5. The method according to claim 1, wherein the pressure of the forwarded stream is reduced by at least 100 psig to vaporize the unreacted alcohol.

6. The method according to claim 1, wherein the flash vessel operates a temperature of from 100° F to 275° F.

7. The method according to claim 1, wherein the forwarded stream is maintained at a pressure of at least 50 psig until the pressure is reduced to vaporize the alcohol.

8. The method according to claim 1, wherein the forwarded stream is maintained at a pressure in the range of from 100 psig to 250 psig until the pressure is reduced to vaporize the alcohol.

9. The method according to claim 1, wherein the forwarded stream is maintained at a temperature in the range of from 150° F. to 350° F.

10. The method according to claim 1, wherein the glycerol enriched stream is forwarded to the flash vessel.

11. The method according to claim 1, wherein the fatty acid ester enriched stream is forwarded to the flash vessel.

12. A method of recovering unreacted alcohol from biodiesel product streams formed in biodiesel ester reactors, said method including the steps of:
   (a) reacting triglyceride and methanol in a first reaction zone under pressure to form an intermediate mixture comprising glycerol, unreacted reactants, and fatty acid methyl ester product;
   (b) treating the intermediate mixture with a separation means to generate a first glycerol enriched stream and a first fatty acid methyl ester enriched stream, and passing the first fatty acid methyl ester enriched stream to a second reaction zone;
   (c) reacting the first fatty acid methyl ester enriched stream with a fresh feed of alcohol in the second reaction zone to form a second intermediate mixture which includes fatty acid alkyl esters, glycerol, and unreacted reactant;
   (d) treating the second intermediate mixture with a second separation means to generate a second glycerol enriched stream and a second fatty acid methyl ester enrich stream;
   (e) forwarding either or both of (i) the first glycerol enriched stream, and (ii) the second fatty acid methyl ester enriched stream to a flash purification vessel which includes a condenser in the upper portion of the vessel;
   (f) reducing the pressure of the forwarded stream in the flash purification vessel and maintaining the temperature of the stream at a level such that the methanol vapor is flashed off of the liquid product stream, thereby producing a methanol-depleted stream;
   (g) condensing the methanol vapor in the condenser, and sequestering the condensed methanol from the methanol-depleted stream; and
   (h) recycling the condensed methanol to at least one of the reaction zones.

13. The method according to claim 12, wherein the flash purification vessel operates at a pressure in the range of –2 to –10 psig.

14. The method according to claim 12, wherein the flash purification vessel further includes a reboiler which heats the methanol-depleted stream.

15. The method according to claim 12, wherein the flash purification vessel includes trays and/or packing material.

16. A continuous method for recovering unreacted alcohol from biodiesel product streams formed in biodiesel ester reactors, said method comprising the steps of:
   a) reacting triglycerides and an excess of alcohol in a pressurized reactor having a pressure of at least 30 psig, and generating a pressurized liquid stream which includes unreacted alcohol;
   b) sequestering the unreacted alcohol from the pressurized liquid stream by selectively vaporizing the alcohol;
   c) condensing the alcohol vapor by heat exchange in a condensing unit with a coolant stream that comprises a pre-reactor triglyceride feedstock, wherein the feedstock coolant stream enters the condensing unit at a first temperature and exits the condensing unit at a second, higher temperature;
   d) forwarding at least a portion of the heated triglyceride feedstock stream to the reactor; and
   e) collecting the condensed alcohol.

17. The method according to claim 16, wherein the pre-reactor triglyceride feedstock includes organic fats, oils, greases, and combinations thereof.

18. The method according to claim 16, wherein the pre-reactor triglyceride feedstock is heated by at least 25° F. in the condensing unit.

19. The method according to claim 16, wherein the pre-reactor triglyceride feedstock is heated to a temperature in the range of from 150° F. to 450° F. in the condensing unit.

20. The method according to claim 16, wherein a portion of the heated triglyceride feedstock stream exiting the condensing unit is sent directly to the reactor and a portion of the heated feedstock stream is sent to storage.

21. The method according to claim 1 wherein, each of the pressurized streams is forwarded to separate flash vessels.

22. The method according to claim 12, wherein both of the streams from step (e) are forwarded to separate flash vessels.

* * * * *